United States Patent [19]

Utsunomiya et al.

[11] Patent Number: 5,183,927
[45] Date of Patent: Feb. 2, 1993

[54] PROCESS FOR THE PREPARATION OF IODOALKYNYL CARBAMATES

[75] Inventors: Atsushi Utsunomiya; Mitsuo Nakamura; Toshiaki Kuwatsuka, all of Mobara; Yoshinori Tanaka, Yokohama, all of Japan

[73] Assignee: Mitsui Toatsu Chemicals Incorporated, Tokyo, Japan

[21] Appl. No.: 868,577

[22] Filed: Apr. 15, 1992

[30] Foreign Application Priority Data

Apr. 16, 1991 [JP] Japan .................................. 3-83673

[51] Int. Cl.$^5$ .......................................... C07C 261/00
[52] U.S. Cl. ..................................... 560/115; 560/22; 560/25; 560/27; 560/33; 560/158; 560/167
[58] Field of Search ................. 560/115, 167, 158, 22, 560/27, 25, 33

[56] References Cited

U.S. PATENT DOCUMENTS 3,769,271 10/1973 Southard ............................. 560/167
3,923,870 12/1975 Singer .................................... 560/24

FOREIGN PATENT DOCUMENTS 14032 8/1980 European Pat. Off. ............ 560/167

OTHER PUBLICATIONS

Larsen et al., "Iodinated 3,5-Diaminobenzoic Acid Derivatives," J. Am. Chem. Soc., vol. 78, pp. 3210-3216 (1956).

Primary Examiner—Michael L. Shippen
Attorney, Agent, or Firm—Millen, White, Zelano and Branigan

[57] ABSTRACT

In preparing an iodoalkynyl carbamate by iodinating an alkynyl carbamate with iodine monochloride in water or a solvent mixture composed of water and an organic solvent in the presence of a base, the iodoalkynyl carbamate can be obtained in a yield of as high as 96 to 98% by using the alkynyl carbamate in a concentration of 5 to 20% by weight, dissolving the iodine monochloride in an aqueous solution of hydrochloric acid or an aqueous solution of an alkali metal chloride (the amount of iodine monochloride used being within the range of 1.0 to 1.2 moles per mole of the alkynyl carbamate and the amount of base used being within the range of 0.95 to 2.00 gram equivalents per mole of iodine monochloride), and carrying out the reaction at a temperature of 10° to 40° C. for a period of 1 to 4 hours.

According to this process, highly pure iodoalkynyl carbamates which are useful as industrial germicides can be prepared with good selectivity and in high yield.

13 Claims, No Drawings

PROCESS FOR THE PREPARATION OF IODOALKYNYL CARBAMATES

BACKGROUND OF THE INVENTION a) Field of the Invention

This invention relates to iodoalkynyl carbamates which are useful as germicides for paints, leather, fibers and the like.

b) Description of the Related Art

U.S. Pat. No. 3,923,870 discloses iodoalkynyl carbamates of the general formula (1)

$$[IC\equiv C-(CH_2)_nOCONH]_mR \qquad (1)$$

where R is a substituted or unsubstituted alkyl, cycloalkyl, aryl or aralkyl group containing 1 to 20 carbon atoms and having a valence of m, and m and n are whole numbers of 1 to 3, and a process for the preparation of such compounds.

The process for the preparation of such compounds comprises the steps of iodinating an alkynol of the general formula (3)

$$kHC\equiv C-(CH_2)_nOH \qquad (3)$$

where n is as previously defined, with iodine to form an iodoalkynol of the general formula (4)

$$IC\equiv C-(CH_2)_nOH \qquad (4)$$

where n is as previously defined, and subsequently reacting the iodoalkynol with an isocyanate of the general formula (5)

$$R(NCO)_m \qquad (5)$$

where R and m are as previously defined.

As an alternative process, Japanese Patent Laid-Open No. 100354/'80 (European Patent No. 0014032) discloses a process comprising the steps of reacting an alkynol of the above general formula (3) with an isocyanate of the above general formula (5) to form an alkynyl carbamate of the general formula (2)

$$[HC\equiv C-(CH_2)_n-OCONH]_mR \qquad (2)$$

where R, m and n are as previously defined, and subsequently iodinating the alkynyl carbamate with an iodinating agent as described below to form a compound of the above general formula (1).

However, the former process has the disadvantage that many of the iodoalkynols formed as intermediate products produce heavy foam and are weakly explosive. Moreover, since iodination is effected by use of iodine, polyiodinated by-products are formed in addition to the iodoalkynol. These by-products cannot be removed in the succeeding step, so that they remain in the finally obtained iodoalkynyl carbamate and cause a reduction in purity.

On the other hand, the latter process is superior to the former one in that polyiodinated by-products are scarcely formed. However, since this process uses an iodinating agent comprising a mixture of sodium hypochlorite and an alkali metal iodide or a mixture of sodium hypochlorite, an alkali metal hydroxide and iodine, the following difficulties are encountered.

In this case, sodium hypochlorite acts as an oxidizing agent for the iodine ions which are formed during iodination or added as a starting material, and thereby produces iodine that is effective in the iodination of alkynyl carbamates. Where sodium hypochlorite is not used as a component of the above-described iodinating agent, a large excess (at least two moles per mole of the alkynyl carbamate) of iodine is required.

Moreover, at relatively high temperatures (e.g., 10° C. or above), sodium hypochlorite acts as an oxidizing agent to convert iodine into hypoiodite ions and further iodate ions, and also acts as a chlorinating agent to form chlorine compounds as by-products.

As described above, the addition of sodium hypochlorite is indispensable for effective utilization of the iodine component. However, since sodium hypochlorite not only oxidizes iodine ions but may act as a chlorinating agent or an oxidizing agent, it is necessary to carry out the reaction at a temperature lower than 10° C. Moreover, sodium hypochlorite involves a problem with stability, in that it tends to be converted into sodium chlorate during storage and thus reduced in purity. Accordingly, the utmost care must be taken in the storage of sodium hypochlorite.

SUMMARY OF THE INVENTION

It is an object of the present invention to provide a process for preparing highly pure iodoalkynyl carbamates with good selectivity and in high yield, not by using an oxidizing agent as described above, but by using an iodinating agent which does not undergo a reduction in purity during storage.

According to the present invention, in preparing an iodoalkynyl carbamate by iodinating an alkynyl carbamate with iodine monochloride in water or a solvent mixture composed of water and an organic solvent in the presence of a base, the iodoalkynyl carbamate can be obtained in a yield of as high as 96 to 98 mole % by using the alkynyl carbamate in a concentration of 5 to 20% by weight, dissolving the iodine monochloride in an aqueous solution of hydrochloric acid or an aqueous solution of an alkali metal chloride (the amount of iodine monochloride used being within the range of 1.0 to 1.2 moles per mole of the alkynyl carbamate and the amount of base used being within the range of 0.95 to 2.00 gram equivalents per mole of iodine monochloride), and carrying out the reaction at a temperature of 10° to 40° C. for a period of 1 to 4 hours.

Thus, the present invention provides a process for the preparation of iodoalkynyl carbamates in which highly pure iodoalkynyl carbamates that are useful as industrial germicides can be prepared with good selectivity and in high yield.

DETAILED DESCRIPTION OF THE INVENTION

As a result of intensive investigation on the above-described problems, the present inventors have found that, in order to iodinate an alkynyl carbamate of the general formula (2)

$$[HC\equiv C-(CH_2)_n-OCONH]_mR \qquad (2)$$

where R is a substituted or unsubstituted alkyl, cycloalkyl, aryl or aralkyl group containing 1 to 20 carbon atoms and having a valence of m, and m and n are whole numbers of 1 to 3, it is effective to use iodine monochloride alone in place of an iodide or iodine that requires an oxidizing agent. The present invention has been completed on the basis of this finding.

Thus, the present invention provides a process for the preparation of iodoalkynyl carbamates of the general formula (1)

$$[IC\equiv C-(CH_2)_n-OCONH]_mR \quad (1)$$

where R, m and n are as previously defined, which comprises iodinating an alkynyl carbamates of the above general formula (2) with iodine monochloride.

The present invention will be more specifically described hereinbelow.

The alkynyl carbamate of the general formula (2), which is used as a starting material, can be obtained by reacting an alkynol of the general formula (3)

$$HC\equiv C-(CH_2)_nOH \quad (3)$$

where n is as previously defined, with an isocyanate of the general formula (5)

$$R(NCO)_m \quad (5)$$

where R and m are as previously defined. This method is well known in the field of urethanes, as described in, for example, Organic Synthetic Chemistry, Vol. 19, No. 11, pp. 775-789 (1961).

Specific examples of the alkynol of the general formula (3) include 2-propyn-1-ol, 3-butyn-1-ol and 4-pentyn-1-ol.

Specific examples of the isocyanate of the general formula (5) include alkyl isocyanates such as methyl isocyanate, ethyl isocyanate, propyl isocyanate, butyl isocyanate, hexyl isocyanate, octyl isocyanate, dodecyl isocyanate and octadecyl isocyanate, and various structural isomers thereof; cycloalkyl isocyanates such as cyclohexyl isocyanate; monocyclic aryl isocyanates such as phenyl isocyanate, 4-chlorophenyl isocyanate, 3,4-dichlorophenyl isocyanate, 2-nitrophenyl isocyanate, 3-nitrophenyl isocyanate and 4-nitrophenyl isocyanate; and diisocyanates such as hexamethylene diisocyanate, methylenebisphenyl diisocyanate and tolylene diisocyanate.

The alkynyl carbamate obtained by the above-described method is usually iodinated by reacting it with iodine monochloride in water or a solvent mixture composed of water and an organic solvent in the presence of a base.

Where the solubility of the alkynyl carbamate in water is low, a solvent mixture comprising a combination of water and an organic solvent which is miscible therewith is used in place of water alone. Specific examples of such organic solvents include methanol and ethanol.

It is desirable that the concentration of the alkynyl carbamate in water or the solvent mixture is within the range of 5 to 20% by weight. If the concentration of the alkynyl carbamate is less than 5% by weight, an undesirable reduction in productivity will result. Even if it is greater than 20% by weight, no significant improvement in productivity will be achieved.

The amount of iodine monochloride used is usually within the range of 1.0 to 1.2 moles, preferably 1.0 to 1.1 moles, per mole of the alkynyl carbamate. If the amount of iodine monochloride used is less than 1.0 mole, the alkynyl carbamate will not be converted completely. Even if it is greater than 1.2 moles, no improvement in yield will be achieved and no additional benefit will be obtained.

Although iodine monochloride may be used as such, it is preferably used by dissolving it in an aqueous solution of hydrochloric acid or an aqueous solution of an alkali metal chloride (such as sodium chloride or potassium chloride). This is because iodine monochloride is stable in an aqueous solution of hydrochloric acid or an aqueous solution of an alkali metal chloride and scarcely undergoes a reduction in purity (or content) even during long-term storage. Although the total amount of iodine monochloride may be added at the beginning, it is preferably added continuously so that the reaction may proceed gently. The addition may be carried out over a period of less than 2 hours.

The base used for the reaction can be an alkali metal hydroxide, an alkali metal carbonate or an alkali metal hydrogencarbonate. Specific examples thereof include lithium hydroxide, sodium hydroxide, potassium hydroxide, sodium carbonate, potassium carbonate and sodium hydrogencarbonate.

The amount of base used is preferably within the range of 0.95 to 2.00 gram equivalents per mole of iodine monochloride. If the amount of base used is less than 0.95 gram equivalent, an undesirable reduction in productivity will result. Even if it is greater than 2.00 gram equivalents, no significant improvement in productivity will be achieved. The base may be added in solid form or in the form of an aqueous solution.

The total amount of the base may be added prior to the addition of iodine monochloride, or the base may be continuously added at the same time as the addition of iodine monochloride. The reaction temperature is maintained within the range of 10 to 40° C. Iodine monochloride is added while the temperature is maintained within this range, and the reaction is allowed to proceed further at the same temperature.

If the reaction temperature is lower than 10° C., the reaction time will be unduly long, while if it is higher than 40° C., an undesirable reduction in yield will result.

Although the reaction time may vary according to the reaction temperature, it usually ranges from 1 to 4 hours. After completion of the reaction, the reacted solution is neutralized. Where the reaction is carried out in the solvent mixture, the organic solvent (e.g., methanol) may be removed by concentration or other technique, or may be left as it is. Thereafter, the resulting iodoalkynyl carbamate is isolated from the reaction mixture by extraction with an organic solvent, such as toluene, which is immiscible with water. The isolated iodoalkynyl carbamate can be obtained in the form of crystals by removing the organic solvent (e.g., toluene). Alternatively, the iodoalkynyl carbamate may also be used directly in the form of a solution in the organic solvent (e.g., toluene).

The present invention is further illustrated by the following examples. In these examples, all percentages are by weight unless otherwise stated. As to the products, their melting points were measured and their purities were analyzed by high-performance liquid chromatography (HPLC).

EXAMPLE 1

A reactor (having a capacity of 200 ml and fitted with a condenser and a stirrer) was charged with 7.75 g (0.050 mole) of prop-1-yn-3-yl N-n-butylcarbamate and 80 g of methanol, followed by the addition of 8.3 g (equivalent to 0.073 mole) of a 35% aqueous solution of sodium hydroxide. While this solution was cooled to and maintained at 10° C., 30.5 g of a 15% aqueous solution of sodium chloride containing 28% iodine monochloride (equivalent to 0.053 mole) was added thereto over a period of 20 minutes. Furthermore, the solution was reacted at 15° C. for 2 hours. Thereafter, the reacted solution was neutralized with hydrochloric acid and extracted with 40 g of toluene.

The reacted solution was further extracted five times with toluene and the combined toluene extract was dried over anhydrous magnesium sulfate. Finally, the toluene was removed by evaporation under reduced pressure to obtain 13.8 g of 1-iodoprop-1-yn-3-yl N-n-butylcarbamate.

This product had a melting point of 65°-67° C., its yield was 98.3 mole %, and no impurity was detected by its purity analysis.

EXAMPLE 2

The same procedure as described in Example 1 was repeated, except that 13.35 g (0.050 mole) of prop-1-yn-3-yl N-n-dodecylcarbamate was used as the starting material. Thus, there was obtained 19.0 g of 1-iodoprop-1-yn-3-yl N-n-dodecylcarbamate.

This product had a melting point of 54°-56° C., its yield was 96.5 mole %, and no impurity was detected by its purity analysis.

EXAMPLE 3

The same procedure as described in Example 1 was repeated, except that 19.05 g (0.050 mole) of prop-1-yn-3-yl N-cyclohexylcarbamate was used as the starting material. Thus, there was obtained 15.0 g of 1-iodoprop-1-yn-3-yl N-cyclohexylcarbamate.

This product had a melting point of 118°-120° C., its yield was 97.5 mole %, and no impurity was detected by its purity analysis.

EXAMPLE 4

A reactor (having a capacity of 200 ml and fitted with a condenser and a stirrer) was charged with 7.75 g (0.050 mole) of prop-1-yn-3-yl N-n-butylcarbamate and 80 g of methanol. While this solution was cooled to and maintained at 10° C., 30.5 g of a 15% aqueous solution of sodium chloride containing 28% iodine monochloride (equivalent to 0.053 mole), together with a 25% aqueous solution of sodium hydroxide, was added thereto over a period of 20 minutes so as to maintain its pH at 7. Furthermore, the solution was reacted at 15° C. and pH 7 for 2 hours. Thereafter, the methanol contained in the reacted solution was removed by evaporation under reduced pressure. Then, the reacted solution was extracted with 40 g of toluene and the toluene extract was dried over anhydrous magnesium sulfate. Finally, the toluene was removed by evaporation under reduced pressure to obtain 13.6 g of 1-iodoprop-1-yn-3-yl N-n-butylcarbamate.

This product had a melting point of 65°-67° C., its yield was 96.8 mole %, and no impurity was detected by its purity analysis.

EXAMPLE 5

The same procedure as described in Example 1 was repeated, except that the reaction temperature was maintained at 20° C. Thus, there was obtained 13.6 g of 1-iodoprop-1-yn-3-yl N-n-butylcarbamate.

This product had a melting point of 65°-67° C., its yield was 96.8 mole %, and no impurity was detected by its purity analysis.

EXAMPLE 6

The same procedure as described in Example 1 was repeated, except that a mixture of 60 g of ethanol and 20 g of water was used in place of 80 g of methanol. Thus, there was obtained 13.8 g of 1-iodoprop-1-yn-3-yl N-n-butylcarbamate.

This product had a melting point of 65°-67° C., its yield was 98.3 mole %, and no impurity was detected by its purity analysis.

COMPARATIVE EXAMPLE 1

The same procedure as described in Example 1 was repeated, except that 6.66 g (0.026 mole) of iodine was used in place of 28% iodine monochloride (equivalent to 0.053 mole). Thus, there was obtained 7.3 g of 1-iodoprop-1-yn-3-yl N-n-butylcarbamate (in a yield of 52.0 mole %).

Its purity analysis revealed the presence of 1.2% of polyiodinated products (impurities).

COMPARATIVE EXAMPLE 2

The same procedure as described in Example 1 was repeated, except that the reaction temperature was maintained at 50° C. Thus, there was obtained 11.6 g of 1-iodoprop-1-yn-3-yl N-n-butylcarbamate (in a yield of 82.3 mole %).

Its purity analysis revealed the presence of 1.5% of polyiodinated products (impurities).

COMPARATIVE EXAMPLE 3

The same procedure as described in Example 1 was repeated, except that 13.20 g (0.52 mole) of iodine was used in place of 28% iodine monochloride (equivalent to 0.053 mole). Thus, there was obtained 11.9 g of 1-iodoprop-1-yn-3-yl N-n-butylcarbamate (in a yield of 84.7 mole %).

Its purity analysis revealed the presence of 2.5% of polyiodinated products (impurities).

COMPARATIVE EXAMPLE 4

A reactor (having a capacity of 200 ml and fitted with a condenser and a stirrer) was charged with 7.75 g (0.050 mole) of prop-1-yn-3-yl N-n-butylcarbamate and 80 g of methanol, followed by the addition of 8.3 g (equivalent to 0.073 mole) of a 35% aqueous solution of sodium hydroxide. While this solution was cooled to and maintained at 10° C., 6.73 g (equivalent to 0.027 mole) of iodine was added thereto. After 20.5 g of a 6% aqueous solution of sodium hypochlorite was subsequently added thereto, the solution was reacted for 2 hours while its temperature was maintained at 10° C. Thereafter, the reacted solution was neutralized with hydrochloric acid and extracted with 40 g of toluene.

The reacted solution was further extracted five times with toluene and the combined toluene extract was dried over anhydrous magnesium sulfate. Finally, the toluene was removed by evaporation under reduced pressure to obtain 11.4 g of 1-iodoprop-1-yn-3-yl N-n-butylcarbamate.

Its yield was 81.2 mole %, and its purity analysis revealed the presence of 0.5% of polyiodinated products (impurities).

As described above, the process of the present invention makes it possible to prepare highly pure iodoalkynyl carbamates from starting alkynyl carbamates with good selectivity and in high yield.

Specifically, when iodine monochloride was used as an iodinating agent in accordance with the present invention, the yield of the iodoalkynyl carbamate so formed reached a level of as high as 96-99 mole % and no impurity was detected, as shown in Examples 1 to 6. However, in Comparative Examples 1 to 4 that do not fall within the scope of the present invention, the yield of the iodoalkynyl carbamate was as low as 52.0-84.7 mole % and its purity was low as can be seen from the fact that it contained 0.5-2.5% of polyiodinated products. Especially in Comparative Example 1 in which iodine was used as an iodinating agent, the yield of the iodoalkynyl carbamate had a very low value of 52 mole %. Thus, the effects of the present invention in which specific alkynyl carbamates are iodinated with iodine monochloride are obvious.

What is claimed is:

1. A process for the preparation of iodoalkynyl carbamates of the general formula (1)

$$[IC\equiv C-(CH_2)_n-OCONH]_mR \quad (1)$$

where R is a substituted or unsubstituted alkyl, cycloalkyl, aryl or aralkyl group containing 1 to 20 carbon atoms and having a valence of m, and m and n are whole numbers of 1 to 3, which comprises iodinating an alkynyl carbamate of the general formula (2)

$$[HC\equiv C-(CH_2)_n-OCONH]_mR \quad (2)$$

where R, m and n are as previously defined, with iodine monochloride.

2. A process for the preparation of iodoalkynyl carbamates as claimed in claim 1 wherein the alkynyl carbamate of the general formula (2) is obtained by reacting an alkynol of the general formula (3)

$$HC\equiv C-(CH_2)_nOH \quad (3)$$

where n is as previously defined, with an isocyanate of the general formula (5)

$$R(NCO)_m \quad (5)$$

where R and m are as previously defined.

3. A process for the preparation of iodoalkynyl carbamates as claimed in claim 1 wherein the alkynol of the general formula (3) is 2-propyn-1-ol, 3-butyn-1-ol or 4-pentyn-1-ol.

4. A process for the preparation of iodoalkynyl carbamates as claimed in claim 1 wherein the isocyanate of the general formula (5) is methyl isocyanate, ethyl isocyanate, propyl isocyanate, butyl isocyanate, hexyl isocyanate, octyl isocyanate, dodecyl isocyanate, octadecyl isocyanate, cyclohexyl isocyanate, phenyl isocyanate, 4-chlorophenyl isocyanate, 3,4-dichlorophenyl isocyanate, 2-nitrophenyl isocyanate, 3-nitrophenyl isocyanate, 4-nitrophenyl isocyanate, hexamethylene diisocyanate, methylenebisphenyl diisocyanate or tolylene diisocyanate.

5. A process for the preparation of iodoalkynyl carbamates as claimed in claim 1 wherein the alkynyl carbamate of the general formula (2) is iodinated by reacting it with iodine monochloride in water or a solvent mixture composed of water and an organic solvent in the presence of a base.

6. A process for the preparation of iodoalkynyl carbamates as claimed in claim 5 wherein the organic solvent is methanol or ethanol.

7. A process for the preparation of iodoalkynyl carbamates as claimed in claim 5 wherein the concentration of the alkynyl carbamate in water or the solvent mixture composed of water and an organic solvent is within the range of 5 to 20% by weight.

8. A process for the preparation of iodoalkynyl carbamates as claimed in claim 1 wherein the amount of iodine monochloride used is within the range of 1.0 to 1.2 moles per mole of the alkynyl carbamate.

9. A process for the preparation of iodoalkynyl carbamates as claimed in claim 1 wherein the iodine monochloride is used by dissolving it in an aqueous solution of hydrochloric acid or an aqueous solution of an alkali metal chloride.

10. A process for the preparation of iodoalkynyl carbamates as claimed in claim 1 wherein the iodine monochloride is continuously added over a period of less than 2 hours.

11. A process for the preparation of iodoalkynyl carbamates as claimed in claim 5 wherein the base used for the reaction is an alkali metal hydroxide, an alkali metal carbonate or an alkali metal hydrogencarbonate.

12. A process for the preparation of iodoalkynyl carbamates as claimed in claim 5 wherein the amount of base used is within the range of 0.95 to 2.00 gram equivalents per mole of iodine monochloride.

13. A process for the preparation of iodoalkynyl carbamates as claimed in claim 1 wherein the reaction temperature is within the range of 10° to 40° C.

* * * * *